(12) United States Patent
Kal et al.

(10) Patent No.: US 7,446,194 B2
(45) Date of Patent: Nov. 4, 2008

(54) PREPARATION OF PENICILLIN PROCAINE

(75) Inventors: Reddy A. Kal, Glendora, CA (US); Raul Zavala, Pomona, CA (US)

(73) Assignee: Cross Vetpharm Limited, Dublin (IE)

( * ) Notice: Subject to any disclaimer, the term of this patent is extended or adjusted under 35 U.S.C. 154(b) by 298 days.

(21) Appl. No.: 11/201,286

(22) Filed: Aug. 11, 2005

(65) Prior Publication Data

US 2006/0058280 A1    Mar. 16, 2006

Related U.S. Application Data

(60) Provisional application No. 60/600,380, filed on Aug. 11, 2004.

(51) Int. Cl.
*C07D 499/14* (2006.01)
*C07D 499/24* (2006.01)

(52) U.S. Cl. .................................................... 540/323
(58) Field of Classification Search .................. 540/323
See application file for complete search history.

(56) References Cited

U.S. PATENT DOCUMENTS

| | | | | |
|---|---|---|---|---|
| 2,515,898 | A | | 7/1950 | Rhodehamel, Jr. ............ 167/65 |
| 2,712,009 | A | * | 6/1955 | Vindin Deans et al. ...... 540/320 |
| 2,712,010 | A | * | 6/1955 | Vindin Deans et al. ...... 540/320 |
| 2,725,336 | A | * | 11/1955 | Sumner et al. ............... 514/192 |
| 2,739,962 | A | * | 3/1956 | Bardolph ..................... 540/323 |
| 3,022,290 | A | * | 2/1962 | Jurist ........................... 540/323 |
| 2002/0185558 | A1 | | 12/2002 | Lemanczyk .................... 241/5 |

FOREIGN PATENT DOCUMENTS

| | | |
|---|---|---|
| GB | 686693 | 1/1953 |
| GB | 750373 | 6/1956 |
| GB | 792545 | 3/1958 |
| GB | 816239 | 7/1959 |
| GB | 908308 | 10/1962 |
| WO | 2004/032899 | 4/2004 |

OTHER PUBLICATIONS

Process Bulletin, "Pharmaceutical Products", APV Americas—(1999) Homogenizers, SIC 2834, Wilmington, Massachusetts, USA, 2 pages.
Invensys APV, Tell me more about APV, History and Facts, http://www.apv.com/us/eng/aboutus/historyand_facts/History+and+Facts.htm, 2 pages, (2007).
Invensys APV, Process Bulletin, Pharmaceutical Products, SIC 2834, 3 pages, (1999).
Invensys APV, The Modern Art of Engineering, APV Homogenisers Rannie 55/Gaulin 55, Alberslund, Denmark, 2 pages, (2007).

* cited by examiner

*Primary Examiner*—Mark L Berch
(74) *Attorney, Agent, or Firm*—Jacobson Holman PLLC

(57) ABSTRACT

A process for preparing penicillin G procaine comprises the steps of introducing inactive ingredients into a first mixing tank and sterilizing the mixture of inactive ingredients in the first mixing tank. A procaine hydrochloride is dissolved in a second mixing tank, and the contents of the second mixing tank are added to the first mixing tank through a sterile filter. A solution of penicillin G potassium is introduced to the first mixing tank through a sterile filter, and the contents of the first mixing tank are mixed so that the procaine hydrochloride reacts with the penicillin G potassium forming penicillin G procaine. The resulting suspension is transferred through a homogenizer to a holding tank and penicillin G procaine is filled into a container.

9 Claims, 1 Drawing Sheet

PREPARATION OF PENICILLIN PROCAINE

This is a complete application claiming benefit of provisional 60/600,380 filed Aug. 11, 2004.

INTRODUCTION

The invention relates to the preparation of penicillin procaine.

Penicillin G procaine can be produced in situ by the reaction of Procaine hydrochloride and Potassium Penicillin G. The resulting product is an aqueous suspension containing large particles of procaine G penicillin.

It is known to reduce the particle size of the procaine G penicillin using a milling technique or a microfluidiser as described in US 2002/0185558A.

Another process involves the use of raw materials of a specific size range to provide a penicillin procaine product within a desired particle size range, however problems in batch quality can affect the particle size of the final penicillin procaine product.

The invention is directed towards providing an improved method for preparing penicillin procaine.

STATEMENTS OF INVENTION

According to the invention there is provided a process for preparing penicillin G procaine comprising the steps of:
- introducing inactive ingredients into a first mixing tank;
- sterilising the mixture of inactive ingredients in the first mixing tank;
- dissolving procaine hydrochloride in a second mixing tank;
- adding the contents of the second mixing tank to the first mixing tank through a sterile filter;
- introducing a solution of penicillin G potassium to the first mixing tank through a sterile filter;
- mixing the contents of the first mixing tank so that the procaine hydrochloride reacts with the penicillin G potassium forming penicillin G procaine;
- transferring the resulting suspension through a homogeniser to a holding tank; and
- filling penicillin G procaine into a container.

In one embodiment the suspension is transferred under nitrogen through the homogeniser.

The homogeniser is preferably operated at from 4,000 to 10,000 psi, most preferably at from 6,000 to 10,000 psi.

In one embodiment the inactive ingredients comprise water, methylparaben, lecithin, propylparaben, sodium carboxymethylcellulose and povidone.

In one embodiment the mixture of inactive ingredients in the first mixing tank are heated to a temperature of from 55° C. to 65° C., then pH adjusted, and sterilised by heating to from 122° C. to 124° C. and subsequently cooled to about 25° C.

The procaine hydrochloride may be dissolved in a mixture of water, sodium citrate, sodium formaldehyde and sulfoxylate in the second mixing tank.

A solution of penicillin G potassium may be prepared in a third mixing tank prior to delivery into the first mixing tank.

Preferably the pH of the suspension is maintained between 5.0 and 7.5.

The penicillin G procaine prepared by the process of the invention can be formulated with suitable other active ingredients, such as another antibiotic, especially penicillin G benzathine. A penicillin G benzathine and penicillin G procaine formulation is generally in the form of an injectable suspension. Such a formulation may contain one or more suitable buffers, preservatives and suspending agents.

BRIEF DESCRIPTION OF THE DRAWINGS

The invention will be more clearly understood from the following description thereof given by way of example only with reference to the accompanying drawings, in which.

DETAILED DESCRIPTION

Figure 1:
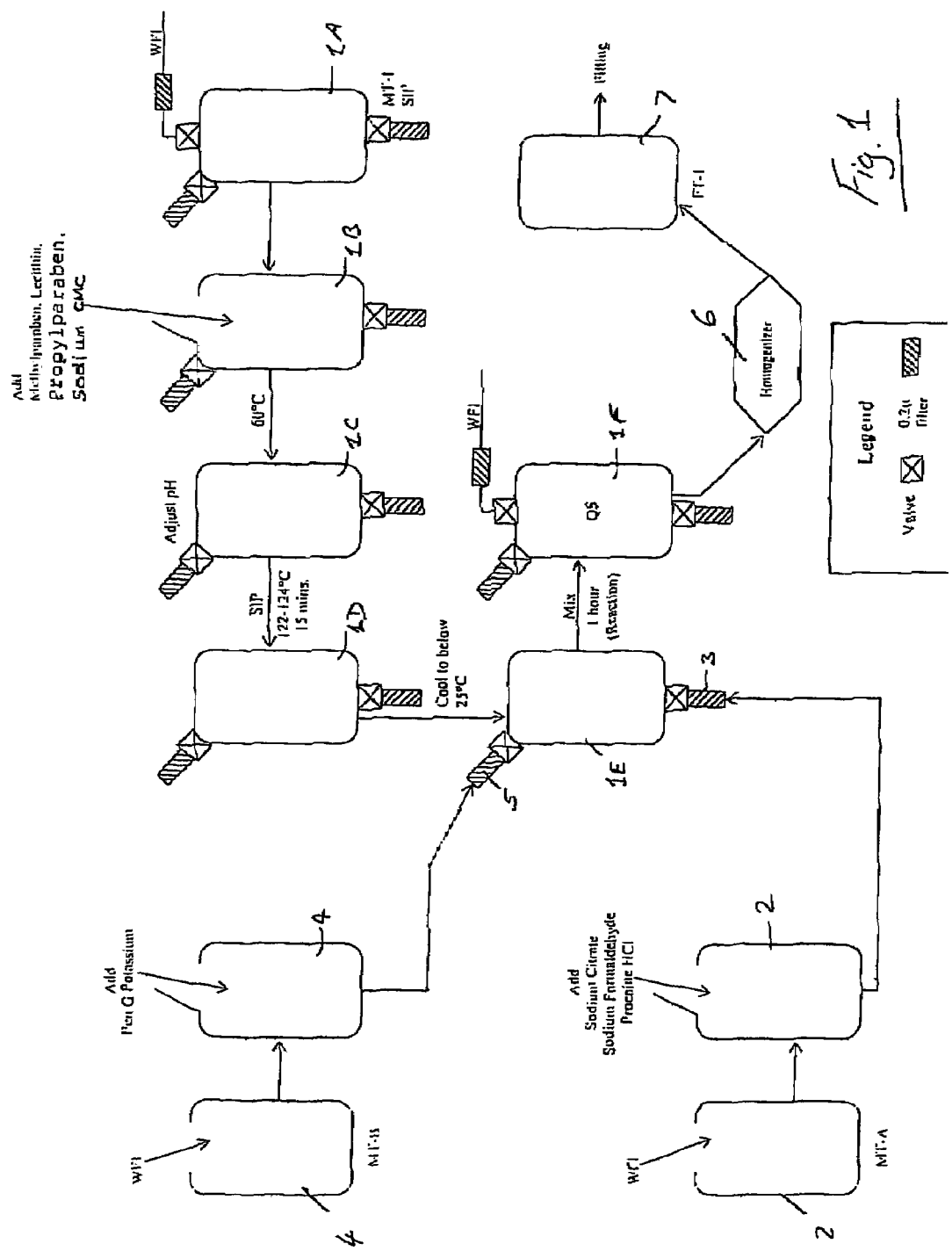
FIG. 1 is a flow diagram of the method for the invention.

The invention provides an improved process for manufacturing a penicillin G procaine injectable suspension.

Using the process of the invention penicillin G procaine may be prepared having a consistent particle size on a large industrial scale.

Penicillin G procaine is prepared by the following method. Water is added in step A to a first mixing tank 1. Inactive ingredients methlyparaben, propylparaben, povidone C-30, lecithin and sodium carboxy cellulose are mixed in the first mixing tank 1 in step B and the solution heated to 58° C. to 65° C., generally about 60° C. The pH is adjusted between pH 5.3 and 6.8 in step C. The solution is then sterilised at 122° C. to 124° C. for a period of about 15 minutes in step D. The solution is cooled to approximately 25° C. in step E.

In a second mixing tank 2 the active ingredients sodium citrate, sodium formaldehyde sulfoxylate, procaine hydrochloride and water for injection are mixed.

The contents of the second mixing tank are added to the first mixing tank through a sterile filter 3. The filter preferably has a 0.2 micron mesh size.

Penicillin G potassium is dissolved in water for injection in a third tank 4 and the solution is added to the first mixing tank through a sterile filter 5. The filter preferably has a 0.2 micron mesh size.

The mixture is mixed for approximately 1 hour to allow the chemical reaction between the penicillin G procaine and procaine hydrochloride to occur. A suspension is formed. Water for injection is added in step F and the suspension is transferred under nitrogen through a homogeniser 6 to a holding tank 7. The homogeniser micronises any large particles of penicillin G procaine formed during the reaction process to form a uniform particle size of penicillin G procaine on a consistent basis.

The homogeniser 6 is an APV Gaulin Homogeniser Model G55. In use, the mixing tank 1 is pressurised with nitrogen until the pressure at the homogeniser inlet is at least 30 psig. The homogeniser 6 is run at a pressure of from 4,000 to 10,000 psi, preferably at from 6,000 to 10,000 psi to achieve optimum particle size distribution at optimum operating efficiency.

The suspension is then aseptically filled into containers for further distribution.

EXAMPLE 1

To prepare a 2000 L batch the following ingredients are used:

|  | Quantity |
| --- | --- |
| Penicillin G Potassium | * |
| Methlyparaben | 2.6 kg |
| Propylparaben | 400 g |

-continued

|  | Quantity |
|---|---|
| Sodium Citrate (dihydrate) | 20 kg |
| Carboxymethylcellulose | 2.0 kg |
| Plasdone C-30 (Povidone) | 10.0 kg |
| Lecithin | 12.0 kg |
| Na Formaldehyde Sulfoxylate | 400 g |
| Procaine Hydrochloride | 40.0 kg+* |
| Water for injection | Q.S. |

*to provide penicillin G procaine, 300,000 U/ml.

Preparation of Bulk

Mixing Tank 1 (MT-1): Mix designated inactive ingredients (Methylparaben, Propylparaben, Povidone C-30, Lecithin and Na Carboxylcellulose) in water for injection and heat the solution to 60° C. Sample the solution for visual observation, pH and bioburden. Adjust the pH if required and SIP sterilise the solution.

Mixing Tank A (MT-A): Mix Sodium Citrate, Sodium Formaldehyde Sulfoxylate and Procaine Hydrochloride in 400 L of water for injection. Take sample for visual observation and bioburden. Transfer into the mixing tank MT1 through 0.2 micron sterile filter.

Mixing Tank B (MT-B): Mix Penicillin G Potassium in 400 L of water for injection. Sample the solution for visual observation and bioburden. Transfer into the mixing tank MT1 through 0.2 micron sterile filter.

Reaction Process

Once all ingredients have been added to mixing tank MT-1, the solution is Q.S.ed to the desired quantity and mixed for a period of not less than 1 hour. At this point the chemical reaction between the ingredients Penicillin G Potassium and Procaine Hydrochloride takes place to produce the active ingredient penicillin G procaine. The mixed solution is the Penicillin G Procaine bulk suspension.

Homogenisation

At the completion of the (1) hour reaction time, the Penicillin G Procaine bulk suspension is transferred, using Nitrogen, to a holding tank through a homogeniser set at not more than 10,000 psi. The homogeniser micronises any large particles of penicillin G procaine formed during the reaction process. The suspension may be held in the holding tank for a period up to twenty four (24) hours prior to aseptically filling into bottles.

Aseptic Filling

The resulting Penicillin G Procaine Suspension is aseptically filled, stoppered and capped into bottles of designated sizes. Quality Control samples are taken for testing at a pre-designated frequency. The finished product bottles are then transported to a cold room (2° C.-8° C.) and quarantined until the completion of all Quality Control testing.

The invention provides a cost effective method for preparing an injectable suspension of penicillin G. procaine of a desired particle size range without compromising the quality of the finished product.

The penicillin G procaine prepared by the process of the invention can be formulated with suitable other active ingredients, such as another antibiotic, especially penicillin G benzathine. A penicillin G benzathine and penicillin G procaine formulation is generally in the form of an injectable suspension. Such a formulation may contain one or more suitable buffers, preservatives and suspending agents.

The invention is not limited to the embodiments hereinbefore described which may be varied in detail.

The invention claimed is:

1. A process for preparing a suspension of penicillin G procaine comprising the steps of:
   introducing inactive ingredients into a first mixing tank;
   sterilising the mixture of inactive ingredients in the first mixing tank;
   dissolving procaine hydrochloride in a second mixing tank;
   adding the contents of the second mixing tank to the first mixing tank through a sterile filter;
   introducing a solution of penicillin G potassium to the first mixing tank through a sterile filter;
   mixing the contents of the first mixing tank so that the procaine hydrochloride reacts with the penicillin G potassium forming penicillin G procaine;
   transferring the resulting suspension through a homogeniser to a holding tank; and
   filling the suspension of penicillin G procaine into a container.

2. A process as claimed in claim 1 wherein the suspension is transferred under nitrogen through the homogeniser.

3. A process as claimed in claim 1 wherein the homogeniser is orerated at a pressure of from 4,000 to 10,000 psi.

4. A process as claimed in claim 1 wherein the homogeniser is operated at a pressure of from 6,000 to 10,000 psi.

5. A process as claimed in claims 1 wherein the inactive ingredients are selected from one or more of the group consisting of water, methylparaben, lecithin, propylparaben, sodium carboxymethylcellulose and povidone.

6. A process as claimed in claim 1 wherein the mixture of inactive ingredients in the first mixing tank are heated to a temperature of from 55° C. to 65° C., then pH adjusted, and sterilised by heating to from 122° C. to 124° C. and subsequently cooled to about 25° C.

7. A process as claimed in claim 1 wherein procaine hydrochloride is dissolved in a mixture of water, sodium citrate, sodium formaldehyde and sulfoxylate in the second mixing tank.

8. A process as claimed in claim 1 wherein a solution of penicillin G potassium is prepared in a third mixing tank prior to delivery into the first mixing tank.

9. A process as claimed in claim 1 wherein the pH of the suspension is maintained between 5.0 and 7.5.

* * * * *